US00PP10797P

United States Patent [19]

Egger et al.

[11] Patent Number: Plant 10,797

[45] Date of Patent: Feb. 16, 1999

[54] ASIATIC HYBRID LILY PLANT NAMED 'CEB DANDY'

[75] Inventors: Donald L. Egger, Wilsonville; Edward A. McRae, Sandy, both of Oreg.

[73] Assignee: Cebeco Lilies, Inc., Aurora, Oreg.

[21] Appl. No.: 918,073

[22] Filed: Aug. 25, 1997

[51] Int. Cl.[6] ..... A01H 5/00

[52] U.S. Cl. ..... Plt./87.4

[58] Field of Search ..... Plt./87.4

*Primary Examiner*—Howard J. Locker

*Attorney, Agent, or Firm*—Klarquist Sparkman Campbell Leigh & Campbell, LLP

[57] ABSTRACT

A new and distinct upright Asiatic Lily Hybrid having light yellow flowers with a darker yellow blush and beautiful maroon brushmarks above the nectary of each tepal on genetically dwarf stems with dense foliage. Excellent for pot plant production.

2 Drawing Sheets

BACKGROUND OF THE INVENTION

The present invention relates to a new and distinct cultivar of Lily hybrid referred to commercially as an upright Asiatic hybrid pot lily and given the cultivar name 'Ceb Dandy'. This invention was developed by controlled breeding in Aurora, Oreg., using 77–79, a proprietary, non-released plant as the seed parent, and B-5×BMK, another proprietary, non-released plant as the pollen parent.

This invention has not been observed under all possible environmental conditions. The phenotype may vary significantly with variations in environment such as temperature, light intensity and day length, without, however, any variation in genotype.

The following traits have been repeatedly observed and are determined to be the basic characteristics of this invention which in combination distinguish this lily as a new and distinct cultivar: 1) medium large light yellow flowers with a darker primrose yellow blush and light maroon brushmarks, spots and stigma; 2) large, primrose yellow buds; 3) genetically dwarf stems excellent for pot plant production; 4) very good bud count; 5) good vigor; and 6) good, dense foliage. Bulbs of this plant may be precooled and forced out of season for uniform pot plant production. In addition, this new lily shows good disease resistance.

There are no other pot lilies known to the inventor with this unique coloring.

Asexual reproduction of this new variety has been accomplished at Cebeco Lilies, Inc., Aurora, Oreg., by scaling and tissue culture. The resulting plants have shown that the above-mentioned unique features are stable and reproduce true to type in each successive propagation.

Figure 1:
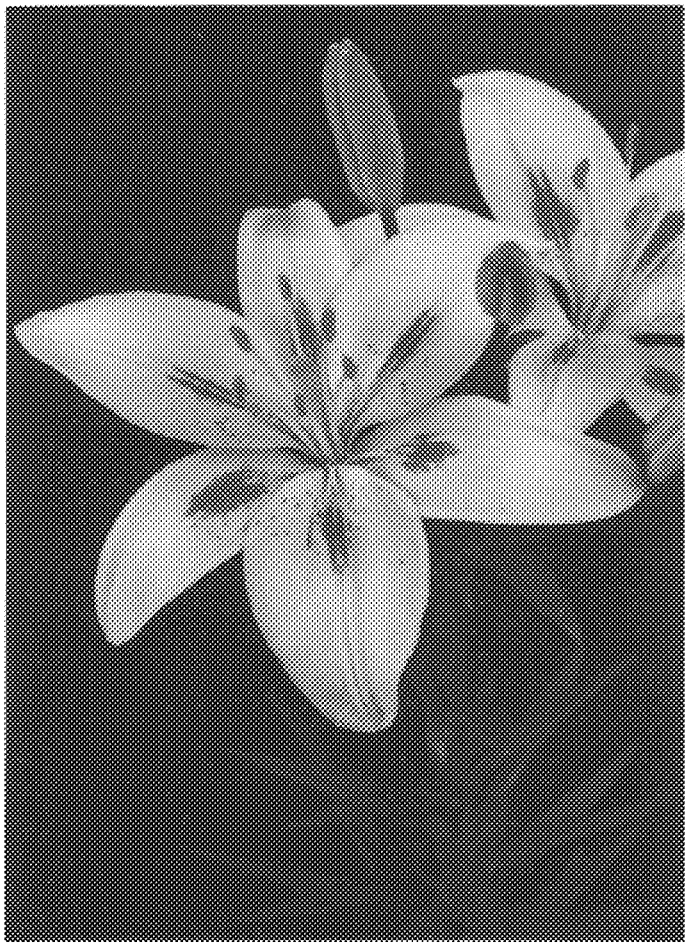
FIG. 1 is a close-up photograph which illustrates in greater detail a single flower of the new plant.
Figure 2:
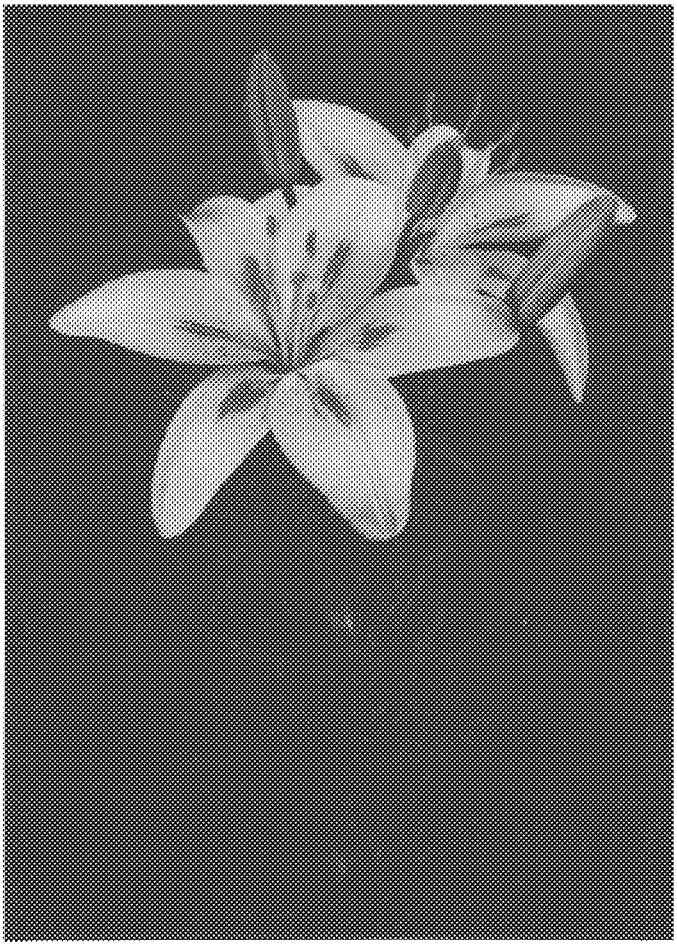
FIG. 2 is a photograph showing the 'Ceb Dandy' lily.

The photographs of the drawing were taken in February 1996 in a studio and illustrate the typical flower and foliage form, with color as true as reasonably possible in this type of color photograph.

DETAILED DESCRIPTION

The following is a detailed description of the invention based on plants produced under commercial practices in the Cebeco Lilies, Inc. greenhouses in Aurora, Oreg. in February 1996 from a very low light growing season. Color references are made to The Royal Horticultural Society Colour Chart, except where the context indicates a term having its ordinary dictionary meaning.

The Plant

Origin: Seedling.

Patentage:

*Seed parent.*—77–79.

*Pollen patent.*—B-5×BMK.

Commercial classification: Hybrid Asiatic lily, pot type.

Classification: Division I-A, Upright Asiatic Hybrid Lily, according to The Horticultural Classification of Lilies by The Royal Horticultural Society of London.

Form: Single erect stem bearing terminal cluster of flowers.

Height: About 74 cm. from the top of the soil to the top of the flowers from bulbs of 12–14 cm. in circumference.

Stem color: Yellow green 144A.

Growth habit: Vigorous, upright and rigid.

Internode length: About 2 to 15 mm.

Foliage:

*Arrangement.*—Spiral.

*Leaf size.*—To about 110 mm. long and 10 mm. wide.

*Leaf shape.*—Lanceolate.

*Texture.*—Leathery.

*Aspect.*—Glossy when mature. May have white hairs when young on margins and in the axils.

*Color.*—Medium green on both sides. Closest to Yellow Green Group 146A with the bottomside slightly lighter.

Bulbs:

*Size.*—Variable, ranging to about 12 to 14 cm. in circumference as used commercially.

*Color.*—White.

The Bud

Size: Large, to about 80 mm. long and 20 mm. wide just prior to opening.

Shape: Ovoid with an obtuse tip.

Rate of opening: The mature bud opens slowly in response to light.

Color: Light yellow. Yellow Group 10B-C overall.

The Flower

Blooming habit: Annually, once and early season.

Days to bloom: Flowers approximately 66 days after spring greenhouse planting under typical commercial flower forcing conditions of 15 degrees Celsius night time temperatures.

Flower size: Medium-large.

*Diameter.*—About 14.5 cm.

*Depth.*—About 3 cm.

Borne: In a raceme of 4 to 5 flowers from bulbs 12 to 14 cm. in circumference.

Shape: When the flower first opens it is bowl shaped. Later the shape flattens out and the tepals reflex slightly at the tips.

Tepalage:

*Number.*—Six.

*Arrangement.*—Imbricated.

*Shape.*—Ovate.

*Texture.*—Spongy, thick.

*Aspect.*—Satiny.

Size:

*Length.*—About 8.5 cm.

*Width.*—Inner tepals—about 40 mm. Outer tepals—about 28 mm.

*Depth of imbrication.*—About 6 mm.

*Nectary.*—2 cm. long; primrose yellow with white glandular pubescence; channels together.

*Projections.*—None.

*Spots.*—Few, oval, around the nectary, mostly on the inner tepals. Greyed-Purple Group 185B.

*Blush.*—Primrose yellow (8B) with a maroon brushmark (185B) above the nectary. The brushmark on the inner tepals is narrower and longer than on outer tepals.

*Color.*—Topside: Light yellow 12C to 8B, intensifying at the blush with brushmark and spots as described above. The yellow color is lighter if grown warmer. Bottomside: Yellow 12C.

*Discoloration.*—Lightens with age.

*Fragrance.*—None.

Pedicle:

*Length.*—About 7 to 8 cm.

*Color.*—Yellow green 144A.

*Orientation.*—Ascending upwardly in a curve to about 45 degrees from the horizontal.

The Reproductive Organs

Stamens:

*Number.*—Six, typical of the genus Lilium.

*Anthers before dehiscence.*—Size: About 15 mm. Color: Light orange brown. Greyed-Orange Group 164B.

*Filaments.*—Length: About 52 mm. Color: Light yellow. Yellow Group 11D.

*Pollen.*—Color: Rust. Greyed Orange 167A.

Pistil:

*Number.*—One.

*Sytle.*—Length: About 35 mm. Color: Yellow green. Yellow green 154C.

*Stigma.*—Color: Greyed Red 181C.

The Fruit

Fertility: Fertile. Shape: Ovoid. Color at maturity: Soft brown.

We claim:

1. A new and distinct cultivar of Asiatic hybrid lily plant substantially as herein shown and described.

* * * * *